US010241080B2

(12) United States Patent
Komai et al.

(10) Patent No.: US 10,241,080 B2
(45) Date of Patent: Mar. 26, 2019

(54) MAGNET EVALUATION DEVICE AND METHOD

(71) Applicant: Nissan Motor Co., Ltd., Yokohama, Kanagawa (JP)

(72) Inventors: Tadashi Komai, Yamato (JP); Yutaka Suzuki, Ebina (JP); Kiyoshi Yoshida, Atsugi (JP); Kohei Murota, Kawasaki (JP); Kunitomo Ishiguro, Odawara (JP); Yasuhisa Koike, Fujisawa (JP); Hideo Mogi, Tokyo (JP)

(73) Assignee: Nissan Motor Co., Ltd., Yokohama (JP)

( * ) Notice: Subject to any disclaimer, the term of this patent is extended or adjusted under 35 U.S.C. 154(b) by 1118 days.

(21) Appl. No.: 14/354,689

(22) PCT Filed: Oct. 25, 2012

(86) PCT No.: PCT/JP2012/077594
§ 371 (c)(1),
(2) Date: Apr. 28, 2014

(87) PCT Pub. No.: WO2013/069467
PCT Pub. Date: May 16, 2013

(65) Prior Publication Data
US 2014/0312889 A1    Oct. 23, 2014

(30) Foreign Application Priority Data

Nov. 7, 2011    (JP) .................... 2011-243611

(51) Int. Cl.
*G01N 27/90*    (2006.01)
*H01F 41/02*    (2006.01)

(52) U.S. Cl.
CPC ......... *G01N 27/90* (2013.01); *G01N 27/9026* (2013.01); *H01F 41/0253* (2013.01)

(58) Field of Classification Search
CPC ..................................... G01N 27/90
See application file for complete search history.

(56) References Cited

U.S. PATENT DOCUMENTS 5,041,791 A * 8/1991 Ackerman ........... G01R 33/341
                                                        324/318
5,343,146 A * 8/1994 Koch ..................... G01B 7/105
                                                        324/227
(Continued)

FOREIGN PATENT DOCUMENTS

JP    6-207972 A    7/1994
JP    2003-234225 A    8/2003
(Continued)

OTHER PUBLICATIONS

The Extended European Search Report for the corresponding European patent application No. 12847451.7 dated Feb. 27, 2015.
(Continued)

*Primary Examiner* — Huy Q Phan
*Assistant Examiner* — Adam S Clarke
(74) *Attorney, Agent, or Firm* — Global IP Counselors, LLP

(57) ABSTRACT

A magnet evaluation device is provided for evaluating a magnet having at least two magnetic pieces bonded to an insulating material sandwiched between two adjacent ones of the magnetic pieces. The magnet evaluation device has an excitation coil and a detection coil. The excitation coil is configured to generate a magnetic field that has a size in a range that corresponds to a region including the insulating material. The detection coil has a coil diameter that is smaller than a length of one of the magnetic pieces in a direction in which the magnetic pieces are aligned.

7 Claims, 8 Drawing Sheets

(56) References Cited

U.S. PATENT DOCUMENTS

| | | | | |
|---|---|---|---|---|
| 5,389,876 A | * | 2/1995 | Hedengren | G01N 27/902 324/242 |
| 5,990,688 A | * | 11/1999 | Bourgeois | G01R 33/12 324/240 |
| 6,339,327 B1 | * | 1/2002 | Potiquet | G01N 27/902 324/220 |
| 6,501,267 B1 | * | 12/2002 | Kurokawa | G01N 27/904 324/242 |
| 2003/0025503 A1 | * | 2/2003 | Fanini | G01V 3/28 324/339 |
| 2005/0122099 A1 | | 6/2005 | Imamoto et al. | |
| 2009/0072822 A1 | | 3/2009 | Sun et al. | |
| 2010/0134100 A1 | * | 6/2010 | Decitre | G01N 27/9046 324/241 |
| 2012/0123699 A1 | * | 5/2012 | Kawata | G01N 27/9033 702/35 |
| 2012/0126803 A1 | * | 5/2012 | Goldfine | G01R 33/0064 324/239 |
| 2012/0206151 A1 | * | 8/2012 | Leonov | G01R 31/34 324/546 |

FOREIGN PATENT DOCUMENTS

| | | |
|---|---|---|
| JP | 2009-33958 A | 2/2009 |
| JP | 2009-142081 A | 6/2009 |
| JP | 2010-11579 A | 1/2010 |
| JP | 2010-183692 A | 8/2010 |
| JP | 2010-271178 A | 12/2010 |

OTHER PUBLICATIONS

Ramos, Ribeiro, and Kubinyi, Measuring interface for an ECT System, Electrical Review, Jul. 2011, pp. 266-271, vol. 87, Instituto de Telecomunicacoes, Lisbon Portugal.

Norio Takahashi et al., Analysis of Eddy Current Losses of Segmented Nd—Fe—B Sintered Magnets Considering Contact Resistance, IEEE Transaction of Magnetics, Mar. 2009, 1234-1237, vol. 45 No. 3.

* cited by examiner

MAGNET EVALUATION DEVICE AND METHOD

CROSS-REFERENCE TO RELATED APPLICATIONS

This application is a U.S. National stage application of International Application No. PCT/JP2012/077594, filed Oct. 25, 2012, which claims priority to Japanese Patent Application No. 2011-243611 filed in Japan on Nov. 7, 2011, the contents of which are hereby incorporated herein by reference.

BACKGROUND

Field of the Invention

The present invention relates to a magnet evaluation device for evaluating permanent magnets and the related method; more particularly, the present invention relates to a magnet evaluation device for evaluating the quality of a permanent magnet by detecting the eddy current that is generated in the magnet and the related method.

Background Information

Conventionally, as a device to evaluate the eddy current loss of a magnet, there is a device in which a magnet to be evaluated is put inside of a thermally insulated sample chamber; by applying a magnetic field to this magnet to be evaluated, the temperature is measured with a thermocouple attached to the magnet to be evaluated (for example, Japanese Laid-Open Patent Publication No. 2003-234225). This conventional device evaluates magnets by capturing the eddy current loss as the heat that is generated by that loss.

SUMMARY

In conventional technology, providing a sample chamber that is sufficiently thermally insulated to block the ambient temperature change is necessary in order to capture the eddy current loss as the heat that is generated as a result. Additionally, in order to allow the magnetic field to reach the magnet that is placed in the sample chamber via the sample chamber, a large magnetic field generator becomes necessary.

For this reason, with conventional devices, enlargement of the device was unavoidable, which became one cause of an increasing equipment cost.

Thus, the object of the present invention is to provide a magnet evaluation device with a simpler configuration that can evaluate magnets by detecting the eddy current that is generated in the magnet and to provide a magnet evaluation method using this device.

In order to achieve the above-described object, the magnet evaluation device according to the present invention is provided for evaluating a magnet having at least two magnetic pieces bonded to an insulating material sandwiched between two adjacent ones of the magnetic pieces. The magnet evaluation device comprises an excitation coil and a detection coil. The excitation coil is configured to generate a magnetic field that has a size in a range that corresponds to a region including the insulating material. The detection coil has a coil diameter that is smaller than a length of one of the magnetic pieces in a direction in which the magnetic pieces are aligned.

Additionally, the magnet evaluation method according to the present invention for achieving the above-described object is a magnet evaluation method for evaluating a magnet having at least two magnetic pieces bonded to an insulating material sandwiched between two adjacent ones of the magnetic pieces. The magnet evaluation method comprises generating a magnetic field with an excitation coil such that a magnetic field is produced having a size in a range that corresponds to a region including the insulating material; detecting an eddy current amount in the magnet using a detection coil that has a coil diameter that is smaller than a length of one of the magnetic pieces in a direction in which the magnetic pieces are aligned; and evaluating the magnet by applying a magnetic field generated by the excitation coil to the magnet and determining the magnet to be defective upon detection of the eddy current amount by the detection coil exceeding a preset threshold value for an eddy current amount in which the preset threshold value is obtained in advance from a relationship between an eddy current that is generated in the magnet and a generated heat amount.

Furthermore, the magnet evaluation method according to the present invention for achieving the above-described object is a magnet evaluation method for evaluating a magnet having at least two magnetic pieces bonded to an insulating material sandwiched between two adjacent ones of the magnetic pieces. The magnet evaluation method comprises generating a magnetic field with an excitation coil such that a magnetic field is produced having a size in a range that corresponds to a region including the insulating material; detecting an eddy current amount in the magnet using a detection coil that has a coil diameter that is smaller than a length of one of the magnetic pieces in a direction in which the magnetic pieces are aligned; moving the magnet within the magnetic field that is generated by the excitation coil, detecting an eddy current amount in the magnet using a detection coil that has a coil diameter that is smaller than a length of one of the magnetic pieces in a direction in which the magnetic pieces are aligned; and evaluating the magnet and determining the magnet to be defective when there is a singular point in changes in an eddy current amount detected by the detection coil.

The excitation coil is configured to generate a magnetic field that has a magnitude in a range that corresponds to the region including the insulating material between at least one magnetic piece of a magnet in which plural magnetic pieces are bonded to sandwich an insulating material (the magnet to be evaluated) and another magnetic piece that is adjacent to this magnetic piece; the coil is configured so that the coil diameter of the detection coil is smaller than the length of one magnetic piece in the direction in which the plurality of magnetic pieces is aligned. With this, only the eddy current that is generated in one magnetic piece in the magnet to be evaluated is directly and reliably detected. Since the eddy current is directly detected in this way, covering the sample chambers with a heat insulating material as is conventional becomes unnecessary, and the device can be miniaturized.

BRIEF DESCRIPTION OF THE DRAWINGS

Referring now to the attached drawings which form a part of this original disclosure.

DETAILED DESCRIPTION OF THE EMBODIMENTS

Figure 1:
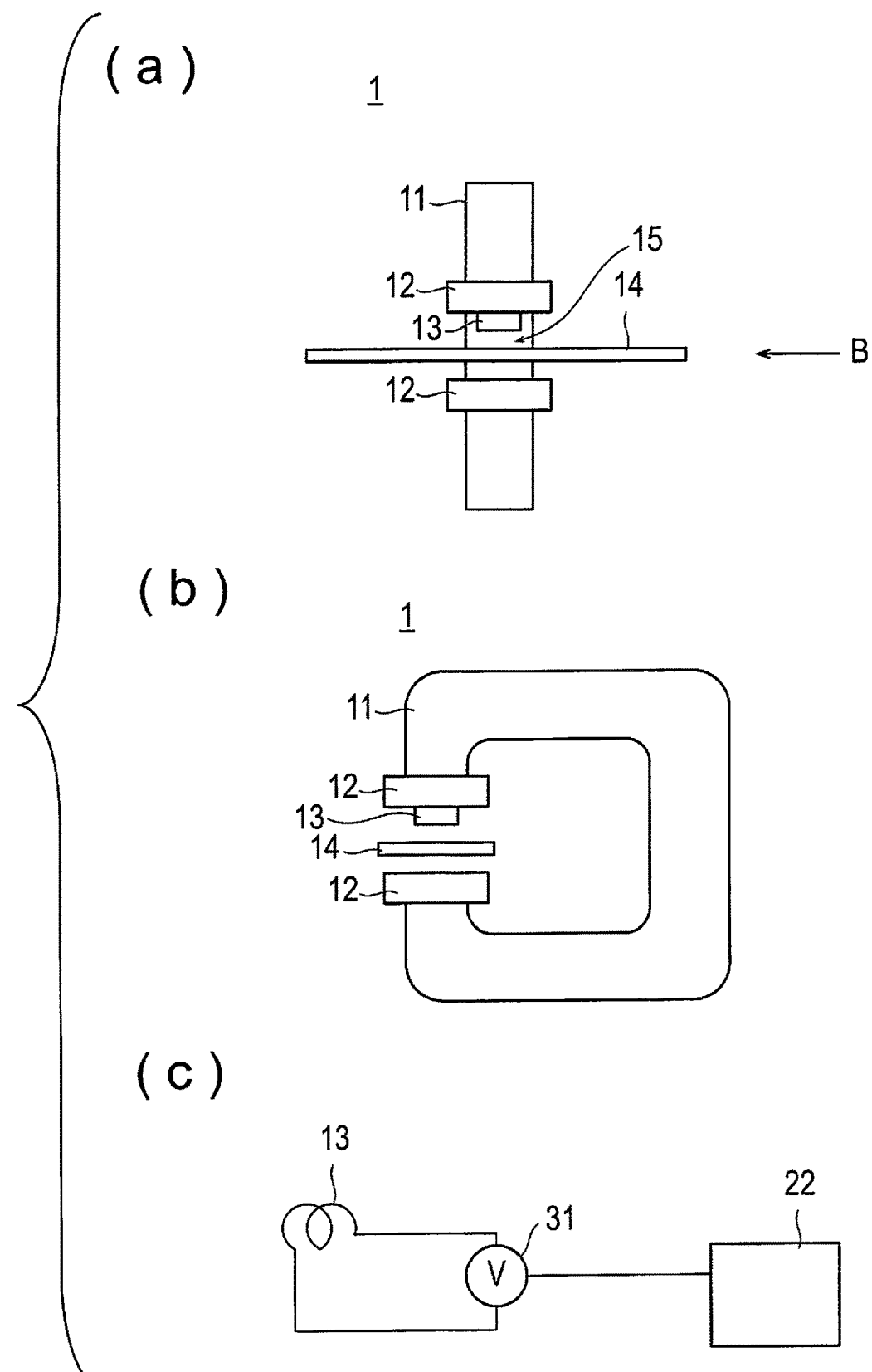
FIG. 1 is a plurality of diagrammatic views that explains the configuration of a magnet evaluation device to which the present invention is applied; view (a) is the frontal view, view (b) is a side view as viewed from the direction of arrow B in views (a), and (c) is a block diagram of the detection coil system.

Embodiments of the present invention will be explained below with reference to the attached drawings. The same elements are given the same reference symbols in the explanation of the drawings, and redundant explanations have been omitted. Additionally, the proportions and sizes of each member in the drawings are exaggerated as a matter of convenience of description and can be different from the actual proportions and sizes.

FIG. 1 is a plurality of diagrammatic views that explains the configuration of the magnet evaluation device to which the present invention is applied. View (a) is the frontal view. View (b) is a side view as viewed from the direction of the arrow B in FIG. view (a). View (c) is a block diagram of the detection coil system.

This magnet evaluation device 1 comprises a C-shaped yoke 11, an excitation coil 12, and a detection coil 13. The device also comprises a conveyor 14 that moves the magnet to be evaluated continuously in the split part of the C-shape of the yoke 11. Additionally, voltage meters 31 (refer to view (c) of FIG. 1) are connected to both ends of the coil wires of the detection coil 13. The measured value of the voltage meter 31 is input into a computer 32 (refer to view (c) of FIG. 1) for determining the quality of the magnet. The computer 32 is a determining section.

The yoke 11 is for forming a magnetic path. The yoke 11 is an iron core and can be one that is commonly used as a material for forming a magnetic path, such as those that laminate ferrite plates.

The excitation coil 12 is wound around the yoke 11. By applying a high-frequency current (an alternating current) to the excitation coil 12, an alternating current is generated in the split part of the C-shape (the evaluation position 15) via the yoke 11. In order to generate a strong magnetic field efficiently in the evaluation position 15, the excitation coil 12 is wound so as not to protrude from near the split part of the C-shape of the yoke 11 (the split part of the yoke 11).

By passing a magnet to be evaluated through this split part of the C-shape, the magnetic flux of the alternating current generated by the excitation coil 12 passes through the magnet to be evaluated. At this time, an eddy current is generated in the magnet to be evaluated in a direction that cancels the alternating magnetic field.

The high-frequency current applied to the excitation coil 12 can be appropriately set according to the usage of the magnet to be evaluated. For example, when evaluating a magnet used for drive motors for electric vehicles and hybrid vehicles, by applying a high-frequency current with a frequency that corresponds to the maximum rotation speed of the motor and the frequency that corresponds to the harmonic frequency, the eddy current loss of the magnet can be evaluated in a state that is close to the state of being mounted to the motor.

Meanwhile, the voltage of the high-frequency current that is applied to the excitation coil 12, that is, the strength of the alternating magnetic field that is generated, can be any value as long as the voltage is a degree at which the eddy current can be detected by the detection coil 13.

The high-frequency current is continuously applied to the excitation coil 12 as long as the magnet to be evaluated is passing through the evaluation position 15.

The detection coil 13 comprises at least one coil for detecting the eddy current that is generated in the magnet to be evaluated. When the eddy current is generated in the magnet to be evaluated, an induced current is generated in the detection coil 13 by the eddy current. If the voltage meters 31 are attached to both ends of the coil wire of this detection coil 13, they can measure the voltage that is generated in the detection coil 13, and that value becomes the eddy current amount. The loss (the eddy current loss) that is caused by the eddy current causes an exothermic phenomenon. Therefore, by converting the relationship between the eddy current amount (the voltage value) that is applied to the detection coil 13 and the heat value by preparing a calibration curve in advance, the amount of heat generated by the eddy current loss can be estimated from the eddy current amount (described in detail below). Besides using a voltage meter, the current that is generated in the detection coil 13 can be detected, for example, as a current value that is applied to the detection coil by attaching an ammeter. A synchroscope can also be connected to the detection coil 13 so that the voltage fluctuation waveform can be directly observed.

This detection coil 13 is disposed so that there is a clearance at which the coil will not interfere with the continuous movement of the magnet to be evaluated and so that the detection coil is coaxial with the excitation coil 12.

The conveyor 14 (the moving section) is a conveyor belt, etc., and the magnet to be evaluated is put on the conveyor; the conveyor moves continuously at a constant speed so that the magnet to be evaluated passes through the evaluation position 15. This conveyor belt, at least the part that enters the magnetic field, should be formed from a non-magnetic material and a non-conductive material. This is because, if magnetic material or conductive material enters the magnetic field, they will disturb the magnetic field or cause a measurement error in the eddy current that is generated by them. For this reason, for example, rubber and resin material are preferable as the material for the conveyor.

The computer 32 (the eddy current amount determining section and the eddy current change determining section) detects the voltage by the current generated by the detection coil 13 and determines the quality of the magnet to be evaluated. The details of this determining method will be mentioned below, but two determining methods are used. In the first determining method, a calibration curve that shows the correlation between the heating value and the voltage value that is detected by the detection coil 13 is prepared in advance, and a threshold value is set for the voltage value in the calibration curve; the magnet is determined to be defective when the threshold value has been exceeded. In this case, the computer 32 becomes an eddy current amount determining section. In the second determining method, the quality of the magnet to be evaluated is determined according to whether or not there is an anomalous fluctuation from the way that the eddy current changes. In this case, the computer 32 becomes an eddy current change determining section.

The computer 32 is configured to comprise a display and to display the determination results like general computers. The computer can also comprise a communication means and can be connected to a host computer for process management or to a server, etc., for storing the determination results.

Here, the magnet to be evaluated, which is the subject of the evaluation in the present embodiment, will be explained.

Figure 2:
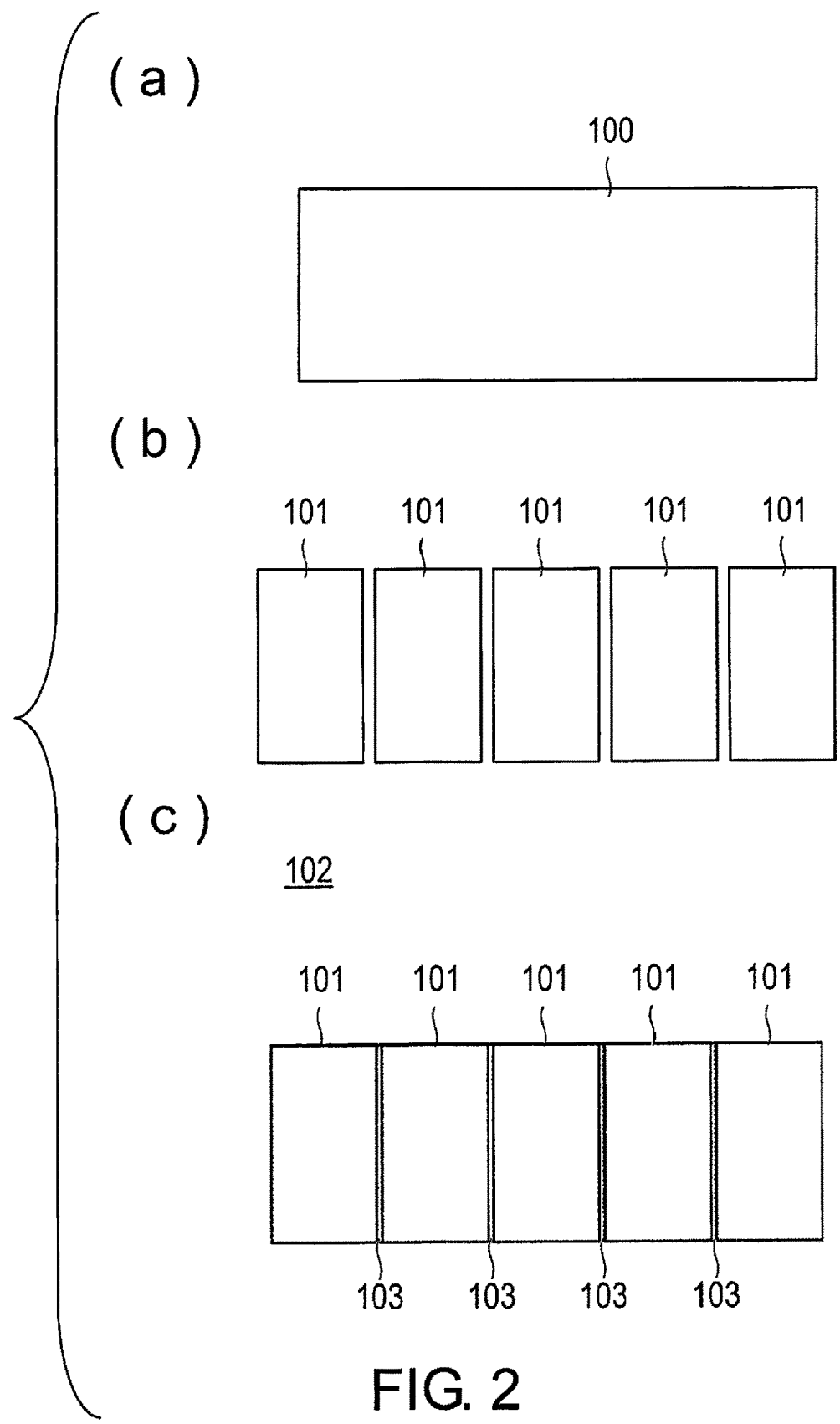
FIG. 2 is a plurality of schematic diagrams explaining the magnet to be evaluated.

FIG. 2 illustrates a plurality of schematic diagrams explaining the magnet to be evaluated.

The magnet to be evaluated, as shown in diagram (a) of FIG. 2, is a magnet 102, in which originally an integrated permanent magnet 100 is divided into a plurality of magnetic pieces 101, as shown in diagram (b) of FIG. 2, after which they are recombined at the dividing surface again, as shown in diagram (c) of FIG. 2. For the bonding, an adhesive agent is applied to the dividing surface to integrate them by bonding. In addition, there are modes in which they are integrated by resin molding after forming an insulating film by oxidizing the dividing surface or by sandwiching an insulating material. Therefore, the magnet to be evaluated is configured to be bonded with magnetic pieces sandwiching an insulating material 103 at the bonding surface, both in the case of bonding and in the case of resin molding. Meanwhile, while obvious, the magnet 102 after bonding is also a permanent magnet An example of a magnet 102 in which one permanent magnet 100 is divided then recombined includes what is disclosed in Japanese Laid Open Patent Application No. 2009-33958 or Japanese Laid Open Patent Application No. 2009-142081. Meanwhile, in the present embodiment, besides magnets that are bonded after dividing what was originally one magnet, such as those disclosed in these publications, a permanent magnet that integrates magnetic pieces that were formed separately via insulating material can be evaluated as well.

Based on the form of the above-described magnet to be evaluated, the relationship between the excitation coil 12 and the detection coil 13 in the magnet evaluation device 1 of the present invention will be explained.

Figure 3:
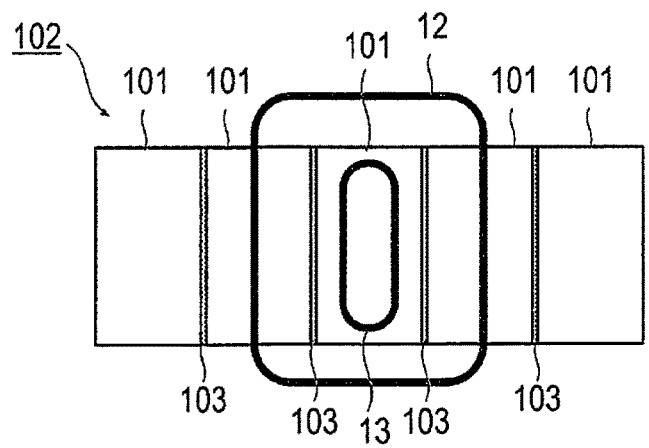
FIG. 3 is a plan view explaining the relationship between the excitation coil and the detection coil.

FIG. 3 is a plan view explaining the relationship between the excitation coil and the detection coil.

The magnet to be evaluated takes an integrated form with a plurality of magnetic pieces 101 being connected as described above. Additionally, in the present embodiment, the eddy current is detected for each individual piece of the integrated plurality of magnetic pieces 101.

The excitation coil 12 needs only to generate an alternating magnetic field that has a magnitude in a range that corresponds to the region including the insulating material 103 between at least one magnetic piece and another magnetic piece that is adjacent to this magnetic piece. By making the excitation coil 12 this size, as shown in FIG. 3, the alternating magnetic field that is generated by the excitation coil 12 will cover the area of the magnetic piece 101 to be evaluated and a part of the adjacent magnetic piece 101. For this reason, the cross section of the yoke 11 (the end surface of the split part of the C-shape) is also made larger than the range including the two adjacent magnetic pieces 101. With this, at least the one magnetic piece 101 to be evaluated and a part of the adjacent magnetic piece 101 can go into the alternating magnetic field, and an eddy current can be generated in the magnetic piece 101 to be evaluated, as well as in the magnetic piece 101 that is adjacent and affects the magnetic piece 101 to be evaluated.

Meanwhile, the magnitude of the alternating magnetic field is not particularly limited, but if too big, the excitation coil 12 will become large and will hinder the miniaturization of the device. Thus, for example, if an alternating magnetic field with a magnitude that is in a range corresponding to the region including two adjacent magnetic pieces 101 is generated, an alternating magnetic field can be applied reliably to one magnetic piece 101 and part of an adjacent magnetic piece 101 to be preferable. In terms of a more specific size of the excitation coil that is required for generating an alternating magnetic field that has a magnitude in the range corresponding to the region including the two adjacent magnetic pieces 101, a range of ⅔-2 times the length of one magnetic piece 101 in the direction in which the magnetic pieces are aligned is preferable (referring to FIG. 5, the size of the excitation coil will be in the range of the length of the magnetic piece 101 in diagram (b) of FIG. 5×1×⅔×1×2). This is because, if the size of the excitation coil 12 is less than ⅔ of the length of one magnetic piece 101, the magnitude of the magnetic field will not be sufficient; if the coil exceeds twice the length, the size of the device will increase which is not preferable.

Meanwhile, the detection coil 13 is made to be a size that will detect only the eddy current of the magnetic piece 101 to be evaluated from the eddy currents that are generated when the magnetic piece 101 to be evaluated and the adjacent magnetic piece 101 are in a normal state. Specifically, as shown in FIG. 3, the coil diameter of the detection coil is made to be a size that is less than or equal to the length of one magnetic piece 101 to be evaluated in the direction that the magnetic pieces are aligned (referring to FIG. 5, the coil diameter of the detection coil 13 will be less than or equal to the length of the magnetic piece 101×1).

The detection coil 13 is installed on the end surface of the split part of the C-shape of the yoke 11 so as to be coaxial with the excitation coil 12. To be coaxial means that the center of the coil diameter of the excitation coil 12 in the direction in which the magnetic pieces 101 are aligned is in the same location as the center of the coil diameter of the detection coil 13 in the direction in which the magnetic pieces 101 are aligned. By disposing the detection coil 13 and the excitation coil 12 coaxially, the eddy current that is generated in the magnetic piece 101 can be reliably detected. However, while they should be coaxial, a placement error around the thickness of the coil wire is acceptable. Additionally, when manufacturing the actual device, for example, the position of the detection coil 13 can be moved with respect to the position of the excitation coil 12 and can be disposed in a position in which the eddy current can be detected the most.

With this, when the magnetic piece 101 to be evaluated is normal and the adjacent magnetic piece 101 is also normal, the eddy current of only the magnetic piece 101 to be evaluated can be detected. Meanwhile, if either the magnetic piece 101 to be evaluated or the adjacent magnetic piece has an abnormality, since the eddy current will be different from the normal state, the fact that there is an abnormality in the magnet to be evaluated that integrates a plurality of magnetic pieces 101 can be known. The fact that either the magnetic piece 101 to be evaluated or the adjacent magnetic piece 101 has an abnormality refers to a case in which the magnetic piece 101 to be evaluated is normal and the adjacent magnetic piece 101 is abnormal or in which the magnetic piece 101 to be evaluated is abnormal and the adjacent magnetic piece 101 is normal, etc. Furthermore, examples of an abnormality of the magnetic piece 101 include internal cracking or chipping of the outer perimeter of a magnetic piece 101, insulation failure at the bonding surface between the adjacent magnetic pieces, etc. When there are abnormalities like these, the eddy current that is generated in one magnetic piece 101 could be different from other magnetic pieces 101, or a large eddy current can be generated across a plurality of magnetic pieces 101, etc., which can cause significant heat generation.

This detection coil 13 can be configured to install a plurality of them with different coil diameters (the size in the direction in which the magnetic pieces 101 are adjacent). With this, even if the size of the magnetic piece 101 of the magnet to be evaluated changes, an immediate response can be enacted by switching the detection coil to be used according to the size of the magnetic piece 101.

Figure 10:
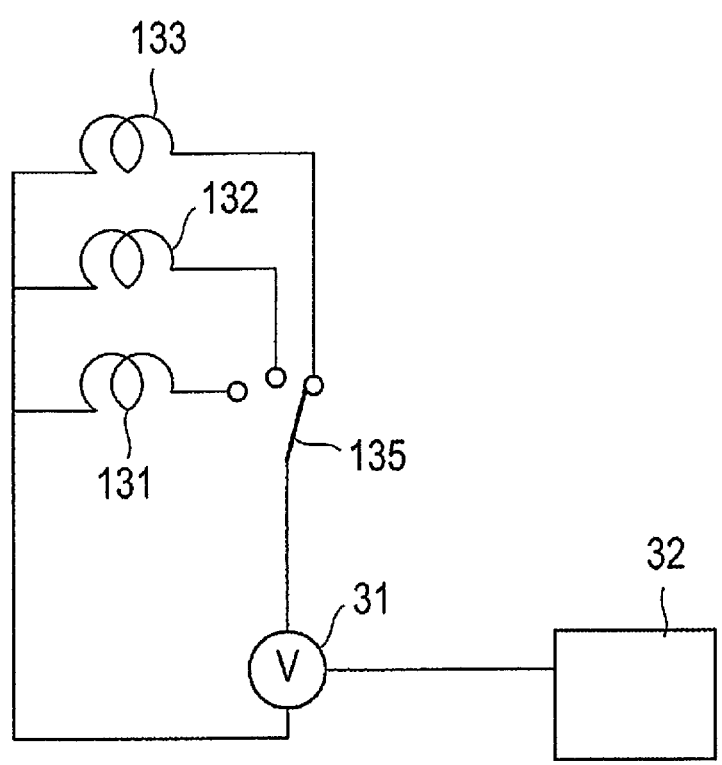
FIG. 10 is a block diagram of the detection coil system when a plurality of detection coils with differing coil diameters is installed.

FIG. 10 is block diagram of the detection coil system when a plurality of detection coils with differing coil diameters are installed. In order to switch the detection coil 13 to be used, for example as shown in FIG. 10, a switch 135 for switching the connection may be installed between the plurality of detection coils 131, 132, and 133 and the voltage meter 31.

Figure 4:
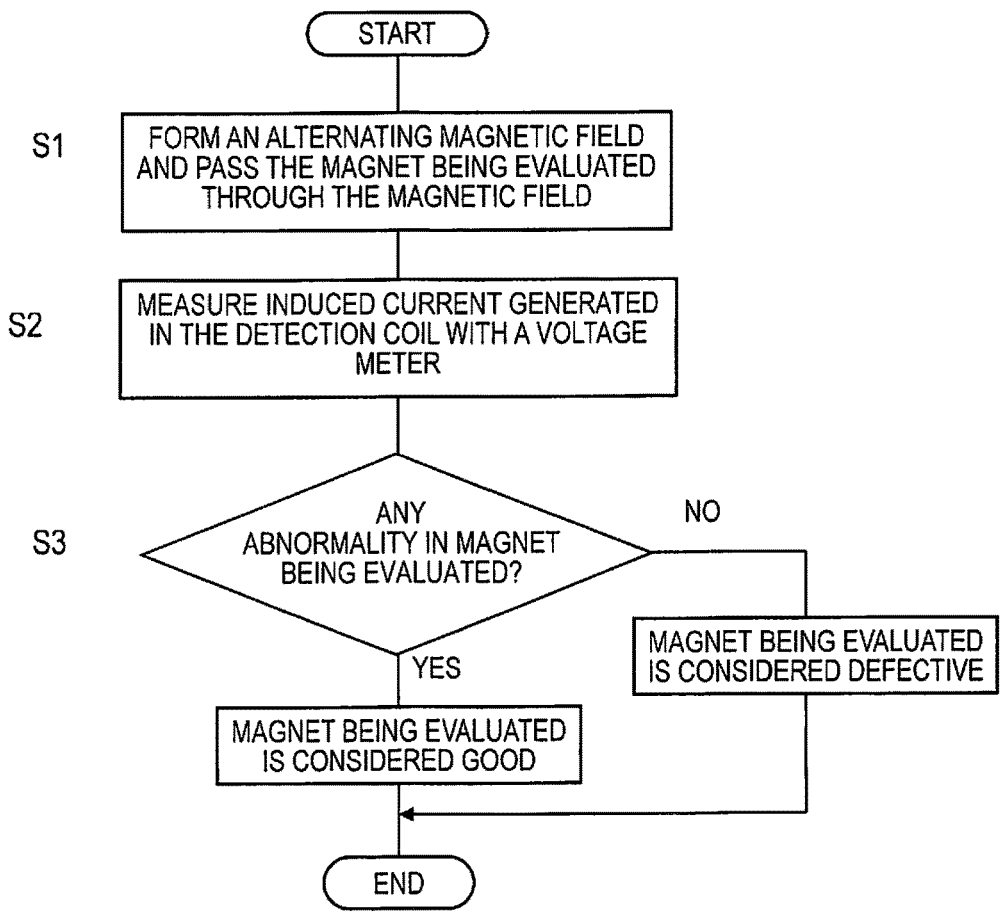
FIG. 4 is a flow chart showing the procedure of the evaluation method.

Next, the evaluation method of the magnet 102 using this magnet evaluation device 1 will be explained. FIG. 4 is a flow chart showing the procedure of the evaluation method.

First, an operator applies a high-frequency wave to the excitation coil 12 to form an alternating magnetic field. Then, the conveyor 14 is operated in this state, and the magnet to be evaluated is passed through in the alternating magnetic field, that is, the evaluating position 15 (S1).

The operator measures the induced current that is generated in the detection coil 13 with the voltage meter 31 while passing the magnet to be evaluated through. The value of the voltage meter 31 is input into the computer 32 (S2). The computer 32 determines the quality of the magnet to be evaluated from the value that is input from the voltage meter 31 (S3). This determination is an evaluation made from the comparison between the voltage of the detection coil and the threshold value and the voltage fluctuation waveform (described in detail below). If there is no abnormality here, the magnet to be evaluated is deemed good (S4). On the other hand, if there is an abnormality, the magnet to be evaluated as a whole is considered to be defective (S5).

The flow of such an evaluation can be controlled by, for example, the computer 32. That is, the computer 32 first activates the excitation coil 12 and the conveyor 14. Then, the computer 32 takes in the value of the induced current that is generated in the detection coil 13 and is measured by the voltage meter 31 and executes the quality determination. Meanwhile, the configuration can be designed so that a computer other than the computer 32 controls the activation, stopping, etc. of the excitation coil 12 and the conveyor 14 and so that the computer 32 only takes in the value of the voltage meter 31 and conducts the determination.

In this way, the magnet evaluation device 1 of the present embodiment is able to continuously conduct an evaluation of the magnet to be evaluated.

EXAMPLES

A trial eddy current evaluation device of the present embodiment was actually manufactured, and an evaluation of a magnet that was bonded after splitting was conducted.

Example 1

In Example 1, the relationship between the size of the magnetic piece 101 and the coil diameter of the detection coil 13 was evaluated.

Figure 5:
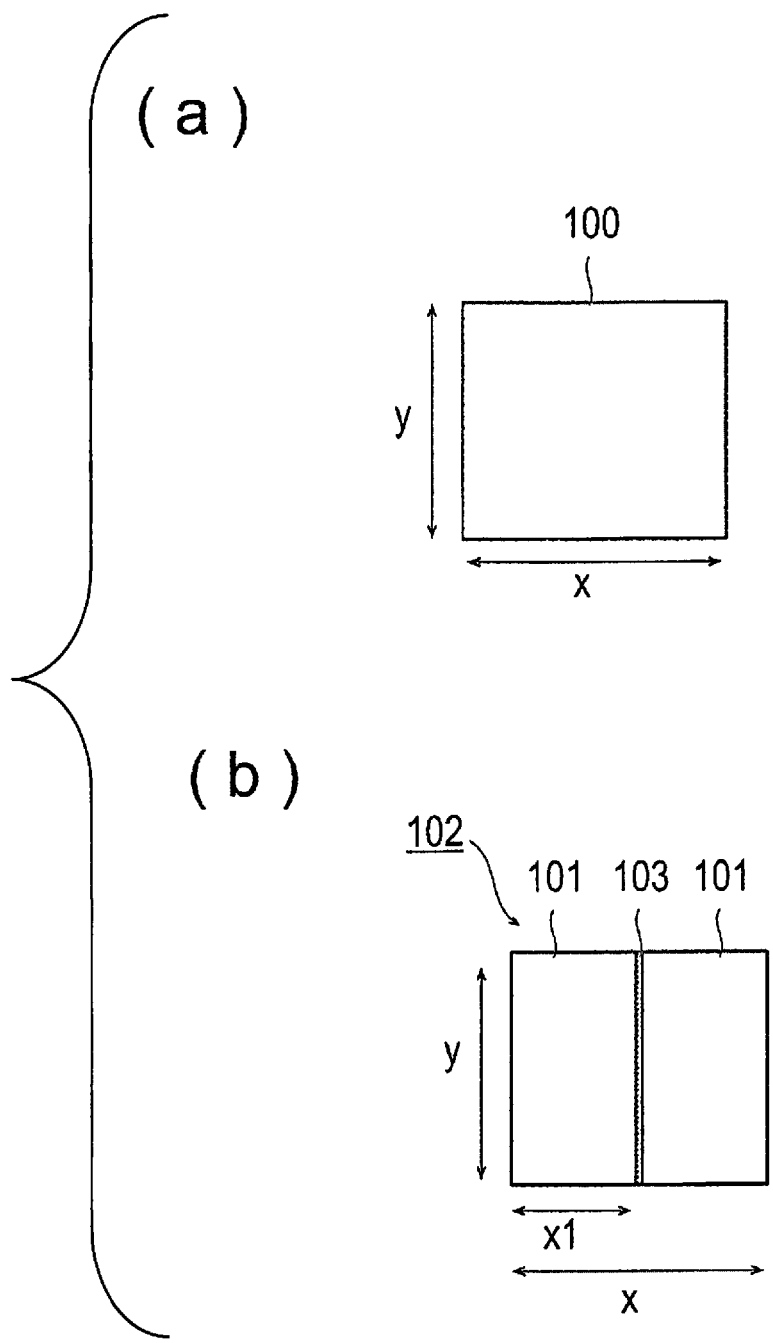
FIG. 5 is a plurality of explanatory diagrams explaining a sample magnet used for the evaluation of Example 1.

FIG. 5 is an explanatory diagram explaining a sample magnet used for the evaluation of Example 1.

Sample 1 (an undivided magnet) is, as shown in diagram of (a) FIG. 5, one permanent magnet 100 that has not been divided. The size is, as diagrammed, 12.4 mm in length (x in the drawing), 21.4 mm in width (y in the drawing), and 2.35 mm in thickness. A plurality of permanent magnets 100 with the same size and same characteristics were prepared as Sample 1.

Sample 2 (a split and recombined magnet) is, as shown in diagram of (b) FIG. 5, a permanent magnet 102 in which a magnet with the same characteristics and same size as Sample 1 was divided in two then recombined by applying an adhesive agent to the entire dividing surface and bonded. The adhesive agent acts as the insulating material 103. Plural magnets were prepared. The plural Sample 2 magnets 102 have a total length after recombination of 12.35-12.5 mm (x in the drawing). The width (y in the drawing) and the thickness were the same as in Sample 1. The length of the magnetic piece 101 after splitting (x1 in the drawing) was 6.15-6.20 mm. The reason why the length x after recombination has changed when compared to Sample 1 is because, since a magnet with the same shape as Sample 1 was divided then bonded with an adhesive agent, the magnet became slightly longer by the amount of coating of the adhesive agent.

Meanwhile, Samples 1 and 2 were checked visually to be sure that none of the plurality of magnets had abnormalities.

The measurement of the eddy current was also conducted while changing the size of the detection coil 13.

A first detection coil is a detection coil 13 whose coil diameter in the direction in which the plurality of magnetic pieces 101 are aligned (the same direction as x in FIG. 5) due to the bonding the split magnetic pieces 101 is larger than the length of one magnetic piece 101. The width direction (the same direction as y in FIG. 5) is smaller than the width of the magnet 102. Specifically, the coil inner diameter is 6 mm in length and 18 mm in width, and the coil outer diameter is 6.3 mm in length and 18.3 mm in width; the coil wire diameter is 0.08 mm, and the number of turns of the coil wire is two turns.

A second detection coil is a detection coil 13 whose coil diameter in the direction in which the plurality of magnetic pieces 101 are aligned (the same direction as x in FIG. 5) due to bonding the split magnetic pieces 101 is smaller than x1 the length of one magnetic piece 101. The width direction (the same direction as y in FIG. 5) is smaller than the width of the magnet 102. Specifically, the coil inner diameter is 1 mm in length and 6 mm in width, and the coil outer diameter is 2.13 mm in length and 7.13 mm in width; the coil wire diameter is 0.08 mm, and the number of turns of the coil wire is eight turns.

The sizes of the excitation coil 12 and the yoke 11 were made so that the entire magnets of Samples 1 and 2 could go inside of the alternating magnetic field that is generated by the excitation coil 12.

Figure 6:
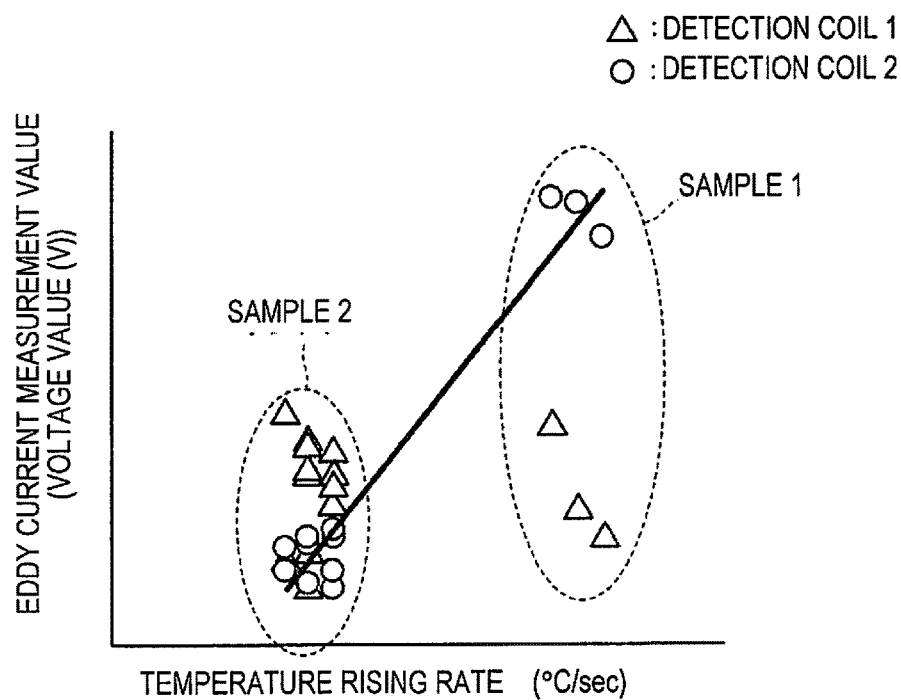
FIG. 6 is a graph showing the correlation between the values of the eddy current measured with the detection coils of different sizes and the temperature change.

FIG. 6 is a graph showing the correlation between the values measuring the eddy current with detection coils 13 of different sizes and the temperature change. The vertical axis is the eddy current measurement value (the voltage value) with the detection coil 13, and the horizontal axis is the temperature rising rate. Measurement of the temperature rising rate was conducted by separately putting a sample whose eddy current had been measured into a vessel that is surrounded by a heat insulating material in the same way as conventional technology (Japanese Laid-Open Patent Publication No. 2003-234225) and applying a magnetic field to the sample; then, the temperature was measured with a thermocouple that is attached to the magnet 102. An eddy current is generated in the magnet 102 by applying a magnetic field; when the temperature rises a certain degree, a saturation temperature will be reached, and the temperature will no longer rise. The temperature rising rate is the value at which the temperature difference from the initial temperature (the room temperature) to the saturation temperature is divided by the time that passed from first applying the magnetic field to reaching the saturation temperature.

In FIG. 6, the triangles are the results due to the first detection coil, and the circles are the results due to the second detection coil.

The temperature rising rate becomes faster as a larger eddy current is generated, and more eddy current is generated with a larger magnet 102 if their characteristics are the same. Therefore, in FIG. 6, the temperature rising rate of those encircled as the Sample 1 group is faster than those encircled as the Sample 2 group.

From the results of FIG. 6, when the first detection coil is used, there is no correlation between the eddy current measurement value and the temperature rising rate. On the other hand, when the second detection coil is used, there is a correlation between the eddy current measurement value and the temperature rising rate, and the temperature rising rates differ according to the detected eddy current measurement value. In other words, with respect to Sample 1, the voltage of the eddy current is concentrated in a part where the temperature rising rate is fast on the positive side. On the other hand, with Sample 2, the voltage of the eddy current is concentrated in the part where the temperature rising rate is slow on the negative side.

From these results, since the size of the coil diameter is larger than one of the magnetic pieces 101 in the adjacent direction of the magnetic pieces 101 with the first detection coil, in the case of the magnet 102 that has been split and recombined like Sample 2, the eddy current for each magnetic piece 101 cannot be separately measured. For this reason, the results show that both Sample 1 and Sample 2 were measured as eddy currents with the same kind of trend.

Meanwhile, since the size of the coil diameter is smaller than one of the magnetic pieces 101 in the adjacent direction of the magnetic pieces 101 with the second detection coil, the eddy current for each magnetic piece 101 can be separately measured. Therefore, differing trends between Sample 1 and Sample 2 are clearly measured.

Additionally, the size of the detection coil 13 was changed to conduct measurement. The detection coil inner diameter length (in the adjacent direction of the split magnetic pieces) is 1 mm, and the width is 12 mm (a third detection coil). The detection coil inner diameter length (in the adjacent direction of the split magnetic pieces) is 1 mm, and the width is 18 mm (a fourth detection coil). Regarding the diameter and the number of turns of the coil wire, both the third and the fourth detecting coil were configured to be the same as the second detection coil, with a coil wire diameter of 0.08 mm, and the number of turns of the coil wire being eight turns. When using these third and fourth detecting coils, the same correlation between the eddy current measurement value and the temperature rising rate as the second detection coil was also present. From this result, the fact that, if the coil diameter of the detection coil 13 is smaller than one of the magnetic pieces 101 in the direction in which the split magnetic pieces 101 are aligned, the size in the width direction (the non-adjacent direction of the magnetic pieces 101) could be any size was revealed.

Example 2

In the same way as the above-described Sample 2, plural samples with the split and recombined mode were prepared with different sizes. In other words, an originally single magnet was divided in two then bonded again with an adhesive agent to make a split bonded magnet 102, and plural samples were prepared by changing only the sizes. These are called Sample 3. Meanwhile, Sample 3 was checked visually to make sure that none of the plurality of magnets 102 had abnormalities.

The plural Samples 3 were put into a vessel that was surrounded by a heat insulating material in the same way as conventional technology (Japanese Laid-Open Patent Publication No. 2003-234225), and the temperature was measured with a thermocouple that is attached to the magnet 102. The strength of the alternating magnetic field at this time was configured to be the same strength and frequency as when a magnet to be evaluated is used for a motor in a vehicle.

Then, the same Sample 3, for which the temperature measurement was conducted, was used to detect the voltage generated in the detection coil 13 by the eddy current, using the second detection coil of Example 1, that is, a detection coil 13 that is smaller than each of the magnetic pieces 101 of Sample 3. Meanwhile, the sizes of the excitation coil 12 and the yoke 11 were made larger than one of the magnetic pieces 101. With this, a size in which all of the magnetic pieces 101 could be evaluated was made, and a part of the adjacent magnetic pieces 101 on both sides would go into the alternating magnetic field generated by the excitation coil 12. The strength of the alternating magnetic field at this time, since the intention is for evaluation purposes only, is weaker than when the magnet to be evaluated is used for a motor in a vehicle, and the strength is made a degree with which an eddy current that is just large enough to be detected by the detection coil 13 is generated in the magnetic piece 101.

Figure 7:
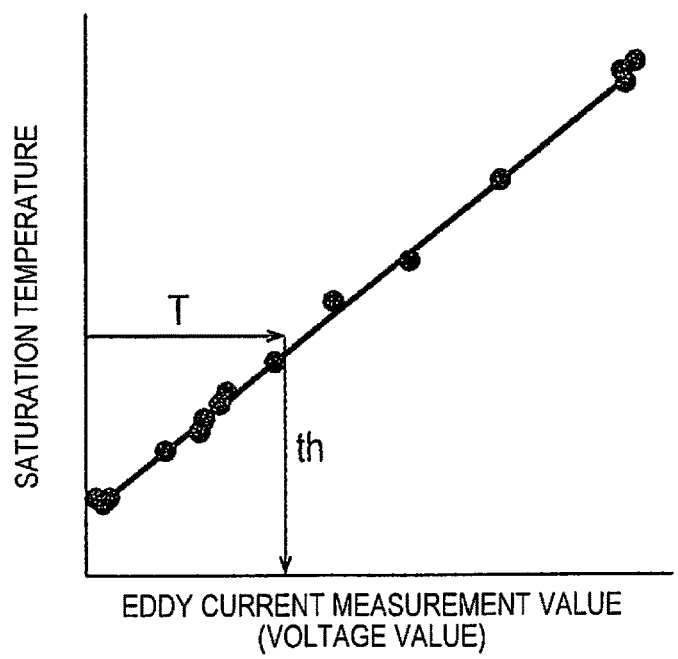
FIG. 7 is a graph showing the relationship between the saturation temperature inside of a vessel surrounded by the heat insulating material that is measured by applying an alternating magnetic field and the voltage that is detected by the detection coil.

FIG. 7 is a graph showing the relationship between the saturation temperature inside of a vessel surrounded by heat insulating material measured by applying an alternating magnetic field and the voltage that is detected by the detection coil. The vertical axis is the saturation temperature, and the temperature is higher the farther up you go. The horizontal axis is the eddy current measurement value (the absolute value of the voltage) of one magnetic piece, and the absolute value of the voltage is higher the farther right you go.

As previously explained, the size of the magnetic piece 101 and the generation amount of the eddy current is such that the latter becomes larger the larger the magnetic piece 101 is, and accompanying this, the heat value also increases. Therefore, the detected saturation temperature becomes larger as the size of the magnetic piece 101 also becomes larger.

As shown in FIG. 7, the larger the eddy current (the voltage) is, the higher the saturation temperature will be. From this, the heat value (the temperature) due to the eddy current loss can be estimated from the measured value (the voltage of the detection coil) of the eddy current.

Using this calibration curve, if a threshold value (th) is provided for the eddy current detection value (the voltage) with an acceptable temperature (T) when actually using the magnet 102, the magnet can be determined to be defective when an eddy current that exceeds this threshold value is detected.

If a calibration curve is prepared in advance by obtaining the correlation between the eddy current amount measured with the detection coil 13 and the heat value in this way, the alternating magnetic field that is generated during the actual evaluation can be just a degree with which the eddy current that is generated in the magnetic piece 101 can be detected with the detection coil 13. For this reason, applying a magnetic field of the same magnitude as the actual usage conditions becomes unnecessary.

Example 3

Figure 8:
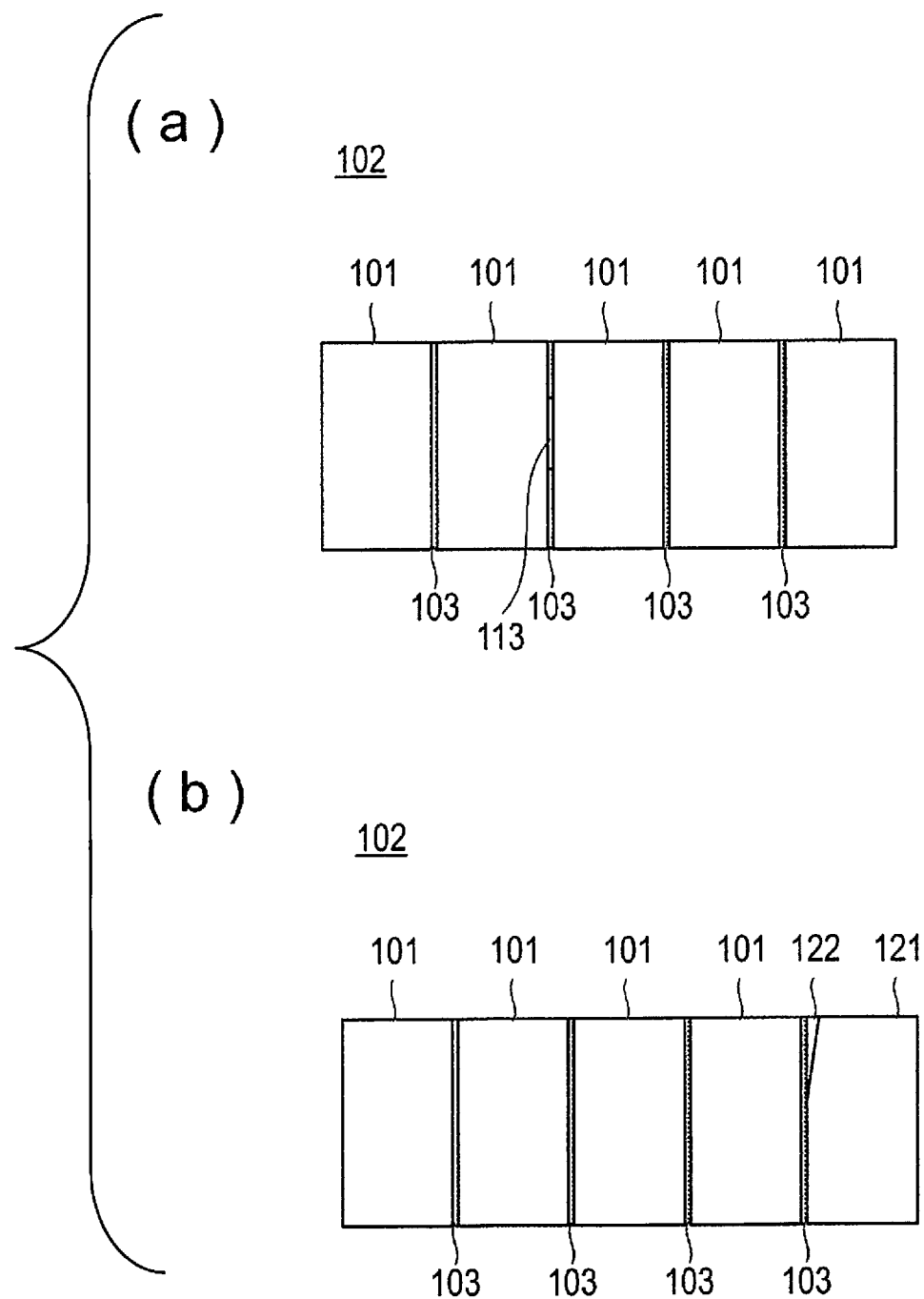
FIG. 8 is a plurality of explanatory diagrams explaining a sample magnet that is used for the evaluation of Example 3.

In Example 3, a magnet with an intentional abnormality was made, and the eddy current was measured. FIG. 8 is a plurality of explanatory diagrams explaining a sample magnet used for the evaluation of Example 3.

Sample 4, as shown in diagram (a) of FIG. 8, is a magnet 102, in which a single permanent magnet was originally divided into a plurality of magnetic pieces 101, after which the dividing surfaces were bonded with an adhesive agent. The adhesive agent acts as the insulating material 103. By partially not applying the adhesive agent connecting the plurality of magnetic pieces 101, one part with an insulation breakdown was created (an insulation breakdown section 113).

In Sample 5, as shown in diagram (b) of FIG., an originally single permanent magnet was divided into a plurality of magnetic pieces 101, and one part of the outer perimeter of one of those magnetic pieces 121 was chipped to create a defective section 122. After the above, the magnet was bonded with the other magnetic pieces 101. The bonded sections do not have insulation breakdown.

For the evaluation, in the same way as the second detection coil of Example 1, using a detection coil that is smaller than one of the magnetic pieces 101 in each sample, the voltage that is generated in the detection coil 13 by the eddy current was measured. Meanwhile, the sizes of the excitation coil 12 and the yoke 11 were made larger than one of the magnetic pieces 101. With this, the size was made such that all of the magnetic pieces 101 to be evaluated and a part of the adjacent magnetic pieces 101 on both sides would go into the alternating magnetic field generated by the excitation coil 12.

Then, with respect to the evaluation position 15 of the magnet evaluation device 1, each sample was continuously moved in the direction in which the plural magnetic pieces 101 are connected, and the voltage value of the detection coil 13 was measured.

Figure 9:
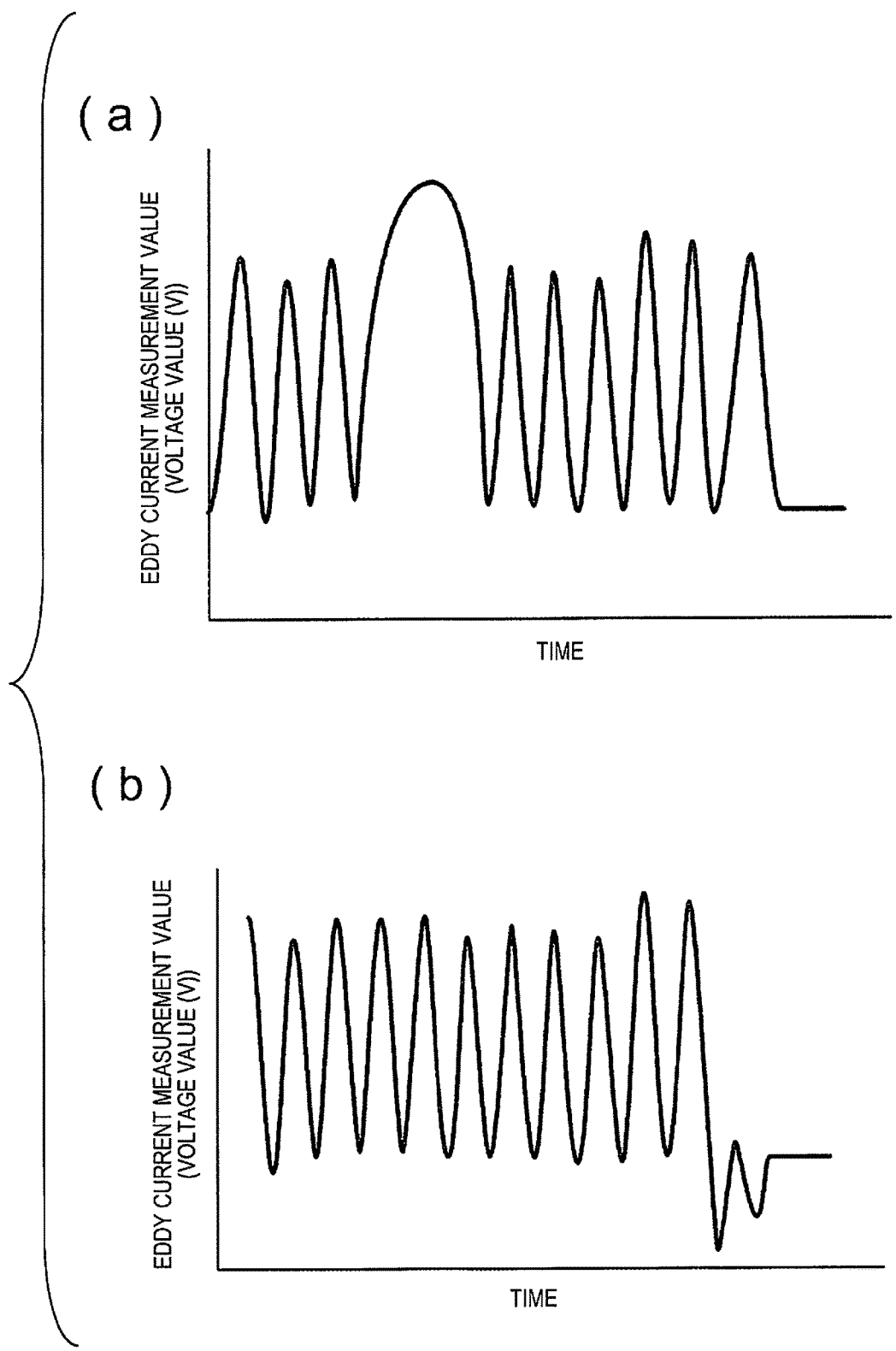
FIG. 9 is a pair of graphs showing the measurement results for the eddy current in Example 3.

FIG. 9 is a graph showing the measurement results for the eddy current in Example 3.

The evaluation results of Sample 4 are shown in graph (a) of FIG. 9. Since Sample 4 is continuously moved, if the voltage of the detection coil 13 is continuously measured, graph in which the measured voltage values change will be generated. This is because Sample 4 is continuously moved, so that the detected eddy current becomes stronger and weaker. The amplitude of each wave is nearly the same, but there are parts where the amplitude becomes large and, as a result, the voltage becomes large. These parts where the amplitude and the voltage value become large match the position of the insulation breakdown section 113 of Sample 4.

The evaluation results of Sample 5 are shown in the graph (b) of FIG. 9. With Sample 5, a graph in which the voltages of the detection coil 13 change is also generated. This is for the same reason as Sample 4 in that, since Sample 5 is continuously moved, the detected eddy current becomes stronger and weaker. The amplitude of each wave is also nearly the same, but there is a part where the voltage becomes small. This part where the voltage becomes small matches the position of the magnetic piece 121 in which the defective section 122 was made on the Sample 5.

Meanwhile, with both Samples 4 and 5, the moving speed of the samples is the same, and the cycle of the graphs (a) and (b) of FIG. 9 (the number of peaks (or valleys) per unit of time) differs depending on the moving speed. If the moving speed is fast, the cycle shown in graphs (a) and (b) of FIG. 9 becomes short (the number of peaks (or valleys) per unit of time increases). On the other hand, if the moving speed is slow, the cycle shown in graphs (a) and (b) of FIG. 9 becomes long (the number of peaks (or valleys) per unit of time decreases).

The actual determination and evaluation are carried out by the computer 32. For this reason, the moving speed, with which the magnet to be evaluated is moved, can be made as fast as the speed at which the computer 32 can perceive changes in the voltage when an induced current is applied to the detection coil 13 due to the eddy current that is generated in the magnetic piece 101. Of course, a person can look at the waveform of the voltage fluctuation and make determinations as well. In this case, the moving speed with which the magnet to be evaluated is moved needs to be a speed at which the detected voltage fluctuation can be perceived by a person as a waveform.

From the results of Example 3, a determination can be made that an abnormality exists when the eddy current is detected while continuously moving the magnet to be evaluated, and there is a singular point in the wave of the voltage change at that time, in other words, if the amplitude fluctuates significantly, or if the detected voltage value fluctuates significantly when compared to the voltage value of the other peaks and valleys.

From the results of Examples 1-3 described above, the evaluation of the split bonded magnets can be conducted in the following way.

First, the coil diameter of the detection coil 13 is made smaller than the magnetic piece 101 in the direction in which each magnetic piece 101 of the split bonded magnet, which is the magnet to be evaluated, is bonded. That is, the size of the detection coil 13 is made to be able detect only the eddy current from one of the magnetic pieces 101 and will not detect the eddy current from the adjacent magnetic pieces 101 (refer to Example 1).

Secondly, the calibration curve is obtained from the relationship between the eddy current amount (the voltage value) that is detected by the detection coil 13 and the heat value (the saturation temperature). Then, a threshold value obtained from the calibration curve is set to the eddy current amount detected by the detection coil 13, and the magnet is determined to be defective when the threshold value is exceeded (refer to Example 2). This is called the first determining method.

Thirdly, the magnet is determined to be defective when there is a singular point in the waveform of the change in the eddy current amount (the voltage value) detected by the detection coil 13 while continuously moving the magnet to be evaluated (refer to Example 3). This is called the second determining method. Meanwhile, regarding the singular point upon evaluation, for example, a recommendation is made to integrate the evaluation results from the many samples and to decide that, when the amplitude and voltage value compared to the other waveforms deviates by a certain percentage point, statistically, an abnormality is considered to be present.

According to the embodiment and examples described above, the following effects are exerted.

(1) When evaluating a magnet 102 that is made by bonding plural magnetic pieces 101 that sandwich an insulating material 103, the excitation coil 12 generates an alternating magnetic field that has a magnitude in a range that corresponds to the region including the insulating material between at least one of magnetic pieces 101 and a magnetic piece 101 that is adjacent to this one magnetic piece 101. Then, regarding the detection coil 13 for detecting the eddy current that is generated in the magnetic piece 101 by this alternating magnetic field, the coil diameter was made smaller than the length of one magnetic piece 101 in the direction in which the plurality of magnetic pieces 101 are aligned. Consequently, only the eddy current that is generated in one magnetic piece 101 in the magnet 102 made by bonding plural magnetic pieces 101 sandwiching an insulating material 103 can be directly and reliably detected. Therefore, since the eddy current is directly detected, the sample chambers covered with heat insulating material as is conventional becomes unnecessary, and the device can be miniaturized. For this reason, the device cost can be reduced.

Additionally, by making the detection coil 13 smaller than one magnetic piece 101, even if plural magnetic pieces 101 are bonded via the insulating material 103, the eddy current that is generated in each one of the magnetic pieces can be reliably detected. Therefore, defects due to an insulation breakdown due to the loss of insulating material between the magnetic pieces, defects due to the loss or cracks (the internal damage) that exist in each one of the magnetic pieces 101, etc., can be detected.

(2) A calibration curve showing the correlation between the eddy current amount (the voltage) detected by the detection coil 13 and the heat value (the saturation temperature) is prepared in advance, and a threshold value of the eddy current amount at which the saturation temperature becomes poor is obtained in advance. The configuration was also designed so that, if the detected eddy current amount exceeded this threshold value, the magnet would be determined to be defective. For this reason, even if the generated eddy current itself is small, the amount of heat generated by the current can be estimated. Therefore, since a strong alternating magnetic field similar to an actual usage state does not have to be applied to the magnet to be evaluated, the excitation coil 12 can be made small, thereby contributing to the miniaturization of the device. Additionally, the fact that the alternating magnetic field can be made weak means that the magnetic field that is generated by the excitation coil 12 is weak. Therefore, shielding peripheral devices from the magnetic field becomes easy, so the device cost as a whole used for the evaluation step, including peripheral devices, can be reduced as well.

(3) An alternating magnetic field is applied while continuously moving the magnet to be evaluated, and the eddy current that is generated at this time is detected by the detection coil 13. The configuration was also designed so that, if there is a singular point in the waveform of the detected eddy current amount (the voltage), the magnet 102 would be determined to be defective. With this, an evaluation can be conducted while continuously moving the magnet to be evaluated. For this reason, when compared to a case, such as conventional technology, in which magnets to be evaluated is put into a thermally insulated sample chamber one by one to be evaluated, the time associated with putting the magnets to be evaluated into and taking them out from the sample chamber becomes unnecessary, so the evaluation time can be substantially shortened. Furthermore, since a defect is determined by finding a singular point in the waveform of the detected eddy current amount (the voltage), a strong alternating magnetic field similar to an actual usage state does not have to be applied to the magnet to be evaluated, and the excitation coil can be miniaturized, so that the device can be miniaturized. Additionally, the fact that the alternating magnetic field can be made weak means that the magnetic field that is generated by the excitation coil 12 is weak. Therefore, shielding peripheral devices from the magnetic field becomes easy, so that the device cost as a whole used for the evaluation step, including peripheral devices, can be reduced as well.

(4) The detection coil 13 was configured to comprise a plurality of coils with differing coil diameters in the direction in which the plural magnetic pieces 101 are aligned and to select one of these plural coils and switch the coil, depending on the length of the magnetic piece 101 to be evaluated, in the direction that the plurality of magnetic pieces 101 are aligned. For this reason, even if the length of the magnetic piece 101 to be evaluated in the direction in which the plural magnetic pieces 101 are aligned is different, detecting the eddy current with the detection coil 13 having the optimum coil diameter becomes possible through a simple switching operation.

(5) A calibration curve showing the correlation between the eddy current amount (the voltage) detected by the detection coil 13 and the heat value (the saturation temperature) is prepared in advance, and a threshold value of the eddy current amount at which the saturation temperature becomes poor is obtained in advance. The configuration was also designed so that, if the detected eddy current amount exceeded this threshold value, the magnet would be determined to be defective. For this reason, even if the generated eddy current itself is small, the amount of heat generated by the current can be estimated. Therefore, since a strong alternating magnetic field similar to an actual usage state does not have to be applied to the magnet to be evaluated, the device can be miniaturized. Additionally, the fact that the alternating magnetic field can be made weak means that the magnetic field that is generated by the excitation coil 12 is weak. Therefore, shielding peripheral devices from the magnetic field becomes easy, so that the device cost as a whole used for the evaluation step, including peripheral devices, can be reduced as well.

(6) The magnet to be evaluated is continuously moved in the magnetic field that is generated by the excitation coil 12, and the configuration was designed such that the magnet is determined to be defective when the change in the eddy current amount detected by the detection coil 13 has a singular point. For this reason, retaining the magnet 102 when evaluating the magnet 102 became unnecessary; therefore, the evaluation time can be shortened. Additionally, since the defect is determined by finding a singular point in the waveform of the detected eddy current amount (the voltage), a strong alternating magnetic field similar to an actual usage state does not have to be applied to the magnet to be evaluated, so the device can be miniaturized. Furthermore, the fact that the alternating magnetic field can be made weak means that the magnetic field that is generated by the excitation coil 12 is weak. Therefore, shielding peripheral devices from the magnetic field becomes easy, so that the device cost as a whole used for the evaluation step, including peripheral devices, can be reduced as well.

The present invention is not limited to the embodiment described above.

For example, a path can also be installed, on which, after the magnet to be evaluated passes through the terminal end of the conveyor, that is, through the evaluating position 15, the good/defective items are separated and transported. Then, with an instruction from the computer 32, the transportation destination of the conveyor 14 is changed to the good item path if the magnet to be evaluated is determined to be good, and to the defective item path if the magnet is determined to be defective. With this kind of configuration, from the insertion of the magnet to be evaluated to the evaluation position 15, the determination of the quality and the selection from the results can all be automated in-line.

Additionally, in the examples, a first determining method that determines the eddy current amount from the threshold value and a second determining method that determines from changes in the eddy current amount by continuously moving the magnet were explained. These evaluation methods can make determinations using both of the determining methods by continuously moving the magnet to be evaluated or by using just one or the other determining method. For example, if both determining methods are used to make a determination, the determination precision will be further improved. Furthermore, the possibility that abnormal exothermic phenomenon due to the eddy current loss would occur can be determined with just the first method. The determination of the loss or internal damage of each one of the magnetic pieces, as well as the determination of insulation breakdown, can also be conducted with just the second determining method.

Meanwhile, when only the first determining method is conducted, determined determination can be made while continuously moving the magnet to be evaluated, or the magnet can be evaluated by temporarily stopping every time a magnetic piece reaches the evaluation position 15. When making a determination while moving the magnet, the magnet is determined to be defective when the absolute value of the fluctuating waveform exceeds a predetermined threshold value. When making a determination while temporarily stopping the magnet, the magnet may be determined to be defective when the eddy current detected at that time exceeds the threshold value.

Besides the above, various modifications can be made to the present invention, based on the configuration recited in the Claims, and those also fall under the category of the present invention.

The invention claimed is:

1. A magnet evaluation device for evaluating a magnet having at least two magnetic pieces bonded to an insulating material sandwiched between two adjacent ones of the magnetic pieces, the magnet evaluation device comprising:
an excitation coil configured to generate a magnetic field that has a size in a range that corresponds to a region including the insulating material;
a detection coil with a coil diameter that is smaller than a length of one of the magnetic pieces in a direction in which the magnetic pieces are aligned; and
an eddy current amount determining section configured to determine the magnet to be defective when an eddy current amount detected by the detection coil exceeds a preset threshold value of the eddy current amount that is obtained in advance from a relationship between an eddy current that is generated in the magnet and a generated amount of heat,
the detection coil being coaxial with the excitation coil.

2. The magnet evaluation device as recited in claim 1, further comprising
a moving section configured to continuously move the magnet in the magnetic field in the direction in which the magnetic pieces are aligned, and
an eddy current change determining section configured to determine the magnet to be defective when there is a singular point in a change of the eddy current amount detected by the detection coil while moving the magnet with the moving section.

3. The magnet evaluation device as recited in claim 2, wherein
the detection coil comprises a plurality of coils with differing coil diameters in the direction in which the magnetic pieces are aligned, and
the eddy current change determining section is further configured to determine whether the magnet is defective by switching between the plurality of coils according to the length of the magnet to be evaluated in the direction in which the plurality of magnetic pieces are aligned.

4. The magnet evaluation device as recited in claim 1, wherein
the detection coil comprises a plurality of coils with differing coil diameters in the direction in which the magnetic pieces are aligned, and
the eddy current change determining section is further configured to determine whether the magnet is defective by switching between the plurality of coils according to the length of the magnet to be evaluated in the direction in which the plurality of magnetic pieces are aligned.

5. The magnet evaluation device as recited in claim 1, wherein
the excitation coil and the detection coil are arranged around a yoke.

6. The magnet evaluation device as recited in claim 1, wherein
the excitation coil comprises two coils arranged on opposite sides of the detection coil.

7. A magnet evaluation method for evaluating a magnet having at least two magnetic pieces bonded to an insulating material sandwiched between two adjacent ones of the magnetic pieces, the magnet evaluation method comprising:
generating a magnetic field with an excitation coil such that a magnetic field is produced having a size in a range that corresponds to a region including the insulating material;
detecting an eddy current amount in the magnet using a detection coil that has a coil diameter that is smaller than a length of one of the magnetic pieces in a direction in which the magnetic pieces are aligned, the detection coil being coaxial with the excitation coil; and
evaluating the magnet by applying a magnetic field generated by the excitation coil to the magnet and determining the magnet to be defective upon detection of the eddy current amount by the detection coil exceeding a preset threshold value for an eddy current amount in which the preset threshold value is obtained in advance from a relationship between an eddy current that is generated in the magnet and a generated heat amount.

* * * * *